United States Patent [19]

Yamaguchi

[11] 4,392,379
[45] Jul. 12, 1983

[54] ULTRASONIC DIAGNOSTIC EQUIPMENT

[75] Inventor: Keiki Yamaguchi, Musashino, Japan

[73] Assignee: Yokogawa Electric Works, Tokyo, Japan

[21] Appl. No.: 231,849

[22] Filed: Feb. 5, 1981

[30] Foreign Application Priority Data

Feb. 12, 1980 [JP] Japan ................. 55-15887

[51] Int. Cl.³ ............................................. G01N 29/00
[52] U.S. Cl. ...................................... 73/626; 128/660
[58] Field of Search ................. 73/626, 613, 620, 625, 73/628, 641; 367/105, 122, 123, 901; 128/660

[56] References Cited

U.S. PATENT DOCUMENTS 4,218,768  8/1980  Hassler ............................... 367/105
4,257,271  3/1981  Glenn ..................................... 73/626

Primary Examiner—Stephen A. Kreitman
Attorney, Agent, or Firm—Parmelee, Bollinger & Bramblett

[57] ABSTRACT

In an ultrasonic diagnostic equipment which irradiates a subject with ultrasonic waves and receives reflected waves responsive thereto so as to provide a tomogram of the subject on the basis of the received signals, two tap-changing type phased arrays having different focal sections are alternately operated during a period of the reception of the reflected waves, and while one of the phased arrays is being operated, the tap changing of the other phased array for altering the focal section is made. In spite of reduced numbers of high-class switches and phased arrays used, spike noise due to the changes-over of switches during the dynamic focusing are prevented.

4 Claims, 5 Drawing Figures

ULTRASONIC DIAGNOSTIC EQUIPMENT

BACKGROUND OF THE INVENTION

This invention relates to improvements in an ultrasonic diagnostic equipment having the dynamic focusing function.

In an ultrasonic diagnostic equipment which irradiates a subject with ultrasonic waves to take tomograms of the subject on the basis of the reflected wave signals, the dynamical changes of the focus of reception for the reflected waves, i.e., the dynamic focusing is (are) made so as to obtain at high resolution all the tomograms of various parts of the subject having unequal depths.

The focusing of the reception is made by properly delaying a plurality of received wave signals and adding the delayed signals by means of a phased array. Therefore, the dynamic focusing is realized in such a way that the individual delay magnitudes of the plurality of received signals in the phased array are altered dynamically in correspondence with the depths of generation of the reflected waves.

The alterations of the delay magnitudes in the phased array are usually made through the tap changing of delay lines which constitute the phased array. For this reason, the alteration of the focus is attended with the change-over of a switch, and a spike noise develops at the change-over of the switch. The spike noise mixes into the received reflected-wave signal and shows an image irrelevant to the subject on a tomogram display, which forms a cause for an erroneous diagnosis. One method for improving such phenomenon is to employ as the change-over switch a high-class switch which generates spike noise. Since, however, the switches for changing the delay magnitudes in the phased array are of a large number, it is uneconomical to replace all the switches with the high-class ones. On the other hand, in case where several phased arrays of unequal focal distances are prepared and are changed-over with switches, the number of the switches to be used is small, and hence, it seems economically unobjectionable to employ high-class switches. Since, however, the phased arrays themselves are far more expensive than the switches etc., it is uneconomical to dispose that number of phased arrays which is equal to the number of foci.

SUMMARY OF THE INVENTION

An object of this invention is to provide an ultrasonic diagnostic equipment which, while reducing the numbers of high-class switches and phased arrays to be used, has eliminated the influence of spike noise due to the change-over of switches during the dynamic focusing.

This invention consists in that two channels of tap-changing type phased arrays having different focal sections which are alternately operated, and that while one of the phased arrays is being operated, the tap changing of the other phased array is made.

DESCRIPTION OF THE PREFERRED EMBODIMENT

Figure 1:
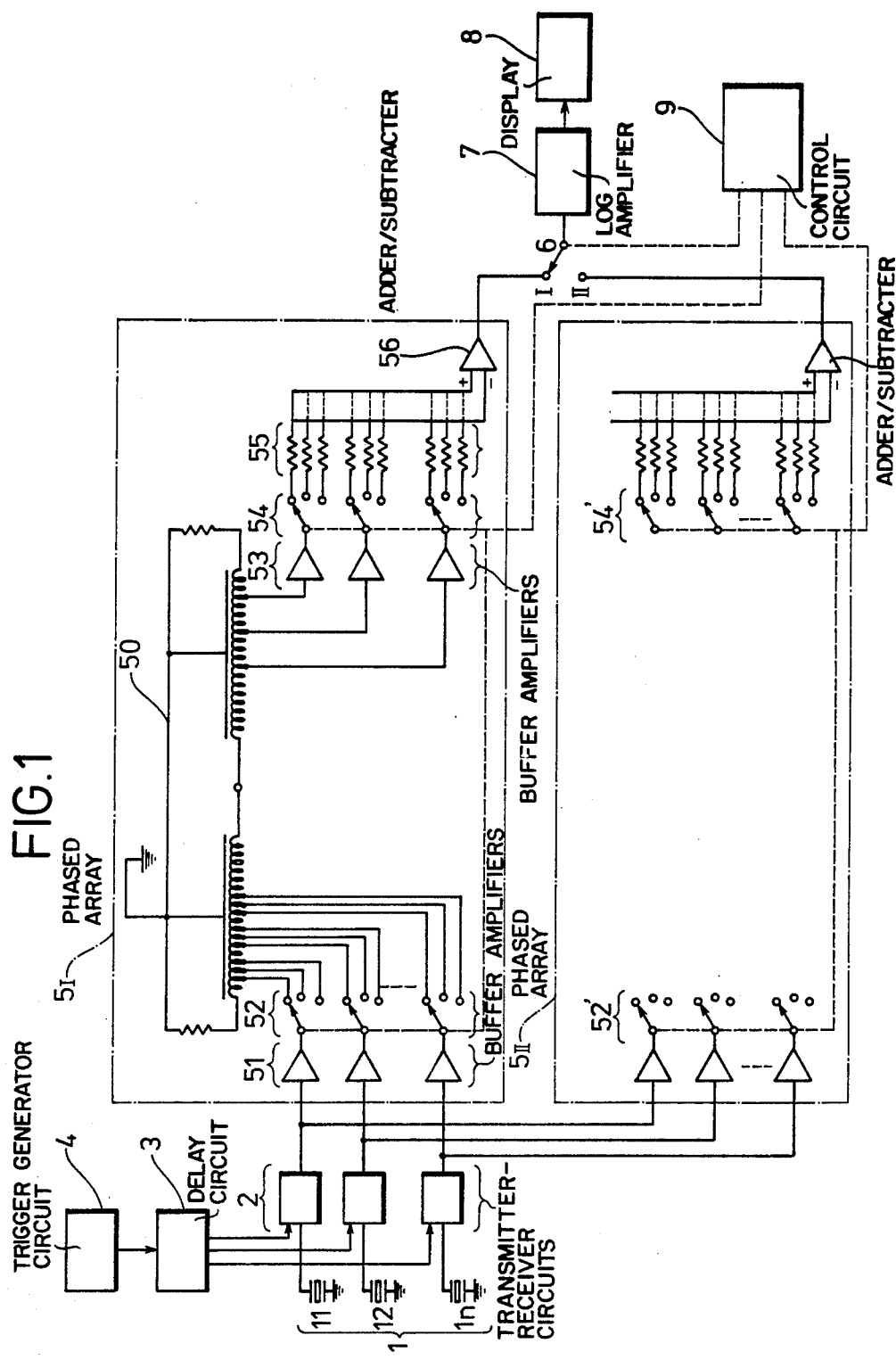
FIG. 1 is a conceptual block diagram of an embodiment of this invention.

Hereunder, this invention will be described in detail with reference to the drawings. FIG. 1 is a conceptual block diagram of an embodiment of this invention. Referring to the figure, numeral 1 designates an array transducer, which includes individual transducer elements 11 - 1n. Numeral 2 designates a group of transmitter-receiver circuits, numeral 3 a delay circuit for transmission, and numeral 4 a transmission trigger generator circuit. Shown at $5_I$ and $5_{II}$ are phased arrays. Numeral 6 indicates a change-over switch, numeral 7 a logarithmic amplifier, numeral 8 a display unit, and numeral 9 a control circuit.

The transmission trigger generator circuit 4 generates transmission trigger signals periodically. The delay circuit for transmission 3 delays the trigger signals in conformity with predetermined directivities of an ultrasonic transmission beam, and then applies them to the group of transmitter-receiver circuits. In accordance with the applied signals, the transmitter-receiver circuits drive the corresponding transducer elements so as to radiate ultrasonic waves into an acoustic field to-be-examined. Reflected waves from the acoustic field to-be-examined responsive to the ultrasonic waves are sensed by the respective transducer elements of the array transducer 1. Among electric signals thus induced in the respective transducer elements, appropriate ones are supplied to the phased arrays $5_I$ and $5_{II}$ via the group of transmitter-receiver circuits 2. That one of the phased arrays $5_I$ and $5_{II}$ which has been selected by means of the switch 6 carries out the directivity composition and filtering of the received signals. The resultant signal is amplified by the logarithmic amplifier 7, and the amplified signal is applied to the display unit 8 and displayed as an image. The change-over switch 6 is changed-over once or several times by the control circuit 9 during the period of the reception of the reflected waves.

The phased arrays $5_I$ and $5_{II}$ have arrangements common to each other, and the details of the arrangement are illustrated as to the array $5_I$. In the phased array $5_I$, numeral 50 indicates an analog delay line which is provided with taps and which has terminating resistances at both its ends. The first half of the delay line 50 is a delaying and adding portion for reception focusing, while the latter half is a transversal filter portion. A group of buffer amplifiers 51 are disposed in correspondence with the group of transmitter-receiver circuits 2, and function to convert output voltages of the corresponding transmitter-receiver circuits into currents. A group of change-over switches 52 are disposed in correspondence with the group of buffer amplifiers 51, and function to apply the output currents of the corresponding buffer amplifiers selectively to the taps of the first half of the delay line. Numeral 53 indicates another group of buffer amplifiers, which function to derive signals from the corresponding taps disposed at equal intervals in the latter half of the delay line 50. Numeral 54 indicates a group of change-over switches, which are disposed in correspondence with the group of buffer amplifiers 53. Numeral 55 indicates a group of weighting resistors, and numeral 56 an adder/subtracter. Output signals from the group of buffer amplifiers 53 are applied to the positive terminal or negative terminal of the adder/subtracter 56 through selected ones of the group of change-over switches 54 and the group of the weighting resistors 55, and they are brought into an algebraic sum which becomes an output signal of the phased array $5_I$.

The various taps of the first half portion of the delay line 50 are set so as to form a plurality of sets of delay times corresponding to a plurality of foci supposed in the acoustic field to-be-examined. By changing these taps by means of the group of change-over switches 52, the dynamic focusing is effected. The various taps of the latter half portion of the delay line 50 and the values of the group of weighting resistances 55 are set so that the impulse response as the transversal filter may become a predetermined characteristic. The characteristic is as stated below.

Figure 2:
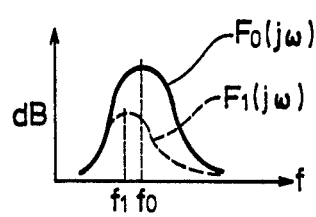
FIG. 2 is a diagram of the spectra of ultrasonic pulses.
Figure 3:
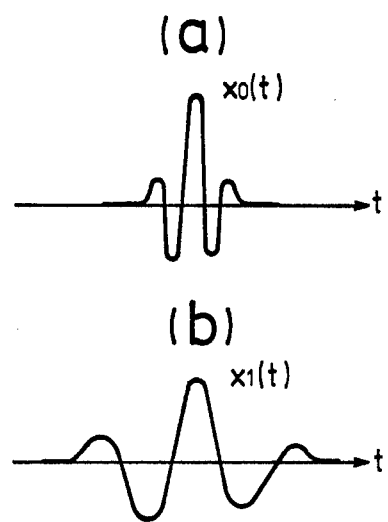
FIGS. 3(a) and 3(b) are waveform diagrams of ultrasonic pulses.

An ultrasonic impulse consists of frequency components in a wide band. In case where such ultrasonic impulse is passed through a living body, the signal attenuation factor versus the distance of passage increases in proportion to the frequency. Regarding the received reflected-wave signals, therefore, one from a deeper part has more higher-frequency components attenuated and becomes a signal with its band narrowed more on the lower-frequency side. This is illustrated in FIG. 2. In correspondence with the spectrum $F_0(j\omega)$ of the transmitted pulse, the spectrum of the received reflected-wave signal from a deep part becomes as shown at $F_1(j\omega)$. In terms of impulse waveforms, a transmitted pulse as shown in FIG. 3(a) returns as a reflected wave as shown in FIG. 3(b). The resolution of a diagnostic picture based on the reflected waves is determined by the center frequency of the band, and it is higher as the center frequency is higher. Accordingly, when on account of the attenuation of the higher-frequency components the band narrows onto the lower-frequency side and the center frequency lowers from the original value $f_0$ to a value $f_1$, the resolution degrades to that extent. In order to prevent the degradation of the resolution, the waveform as shown in FIG. 3(a) may be restored from the received waveform as shown in FIG. 3(b). It has been known that, to this end, a filter may be used which has the impulse response of $$G = \int_{-\infty}^{\infty} \frac{F_0(j\omega)}{F_1(j\omega)} \cdot \epsilon^{-j\omega t} d\omega.$$

Therefore, the positions of the group of taps of the transversal filter and the values of the group of weighting resistances 55 are determined on the basis of the above expression. Since $F_0(j\omega)/F_1(j\omega)$ in the aforecited expression differs depending upon the depth of the reflected wave, the plurality of weighting resistors 55 are prepared in correspondence with depths and are changed-over by the group of change-over switches 54. The change-over of the group of change-over switches 54 is carried out in synchronism with that of the group of change-over switches 52 for the dynamic focusing, and a dynamic filter is realized.

The arrangement of the phased array $5_{II}$ is similar, but the positions of a plurality of foci which it affords are set so as to alternate with the positions of the plurality of foci which the phased array $5_I$ affords. Also in the phased array $5_{II}$, groups of change-over switches 52' and 54' are respectively disposed for the dynamic focusing and the dynamic filter.

Figure 4:
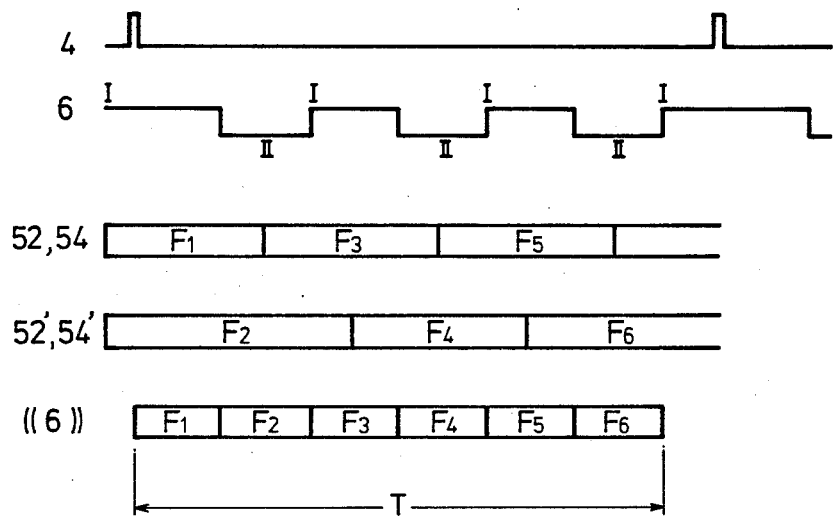
FIG. 4 is a diagram for explaining operations in the equipment of FIG. 1.

The groups of change-over switches 52 and 54, and 52' and 54' in the phased arrays $5_I$ and $5_{II}$ are sequentially changed-over by the control circuit 9 during the period of the reception of the reflected waves. The output ends of the phased arrays $5_I$ and $5_{II}$ are alternately connected to the logarithmic amplifier 7 by the change-over switch 6 during the period of the reception of the reflected waves. The changes-over of the groups of change-over switches 52 and 54, and 52' and 54' are made when the corresponding phased arrays to which they belong are not connected to the logarithmic amplifier 7. More specifically, as illustrated in FIG. 4, assuming that the change-over switch 6 is transferred three cycles during an effective reception period T, the groups of change-over switches 52 and 54 of the phased array $5_I$ are transferred while the change-over switch 6 selects the side of the phased array $5_{II}$, whereas the groups of change-over switches 52' and 54' of the phased array $5_{II}$ are transferred while the change-over switch 6 selects the side of the phased array $5_I$. Owing to such changes-over of the various switches, focused reflected-wave signals are successively received at six focal positions.

In this manner, the groups of change-over switches 52 and 54, and 52' and 54' are transferred while the output ends of the circuits to which they belong are disconnected from the succeeding stage, and hence, spike noise which they generate are not transmitted to the succeeding stage. Accordingly, the groups of change-over switches 52 and 54, and 52' and 54' required in large numbers may be inexpensive switches. On the other hand, the change-over switch 6 always transfers the portions through which the signal currents are flowing, so that a spike noise which it generates mixes into the received signal to bring about an adverse effect. Therefore, only the change-over switch 6 is constructed of a high-class switch which causes little spike noise. This influences the cost of the equipment little because only one such change-over switch is included.

Although the two phased arrays are required, they suffice irrespective of the number of foci. Therefore, this invention is much cheaper than the prior art employing that number of phased arrays which is equal to the number of foci.

As set forth above, this invention is so constructed that two channels of phased arrays having different focal sections which are alternately operated through the changes-over of switches and that while one is being operated, the tap changing of the other is made, and hence, it can realize an ultrasonic diagnostic equipment which is not affected by spike noise due to the changes-over of the switches during the dynamic focusing, in spite of reduced numbers of high-class switches and phased arrays used. In one aspect of performance of this invention, diagnostic pictures of high resolution are obtained irrespective of reflection depths owing to a dynamic filter, and the influence of spike noise due to the tap changing of the dynamic filter is not involved.

I claim:

1. In an ultrasonic diagnostic equipment having an ultrasonic transducer which emits ultrasonic pulses to an acoustic field to be examined and receives reflected ultrasonic waves therefrom for obtaining a tomogram of said acoustic field, said ultrasonic diagnostic equipment including:

first and second channels having phased arrays of different adjustable focal sections means for alternatively operating said first and second channels during the reception of said reflected ultrasonic waves, and switch means for adjusting the focal sections of the phased array of each of said first and second channels when the other of said first and second channels is in operation receiving said reflected waves from said acoustic field whereby tomograms of high revolution are obtained without being influenced by spike noise due to adjustments in the focal sections of the phased arrays.

2. In the ultrasonic diagnostic equipment as claimed in claim 1 in which each of said phased arrays include a dynamic filter whose filtering characteristics are changed by switch means.

3. In the ultrasonic diagnostic equipment as claimed in claim 1 wherein said phased arrays each include a variable delay line and a variable filter.

4. In the ultrasonic diagnostic equipment as claimed in claim 3 in which said variable delay line and said variable filter each including an inductor having a plurality of taps, said taps being selectively varied by said switch means.

* * * * *